United States Patent [19]
Ghodse et al.

[11] Patent Number: 5,784,145
[45] Date of Patent: Jul. 21, 1998

[54] APPARATUS FOR DETERMINING PUPIL DIMENSIONS

[75] Inventors: Abdol Hamid Ghodse; Daniel Robert Stafford Taylor; Alan John Britten, all of London; George Henry Gibson, Sussex, all of Great Britain

[73] Assignee: St. George's Enterprises Ltd.

[21] Appl. No.: 407,003

[22] PCT Filed: Sep. 28, 1993

[86] PCT No.: PCT/GB93/02016

§ 371 Date: Jul. 24, 1995

§ 102(e) Date: Jul. 24, 1995

[87] PCT Pub. No.: WO94/07406

PCT Pub. Date: Apr. 14, 1994

[30] Foreign Application Priority Data

Sep. 28, 1992 [GB] United Kingdom ............ 9220433

[51] Int. Cl.⁶ .................................................. A61B 3/10
[52] U.S. Cl. .................................. 351/205; 351/246
[58] Field of Search ............................ 351/204, 205, 351/200, 246; 33/200; 356/124, 127

[56] References Cited

U.S. PATENT DOCUMENTS

| 3,782,364 | 1/1974 | Watt ............................ 128/2 T |
| 4,834,528 | 5/1989 | Howland et al. ............. 351/211 |
| 5,036,347 | 7/1991 | Tsunekawa et al. .......... 354/400 |
| 5,042,937 | 8/1991 | Cornsweet .................... 351/204 |

FOREIGN PATENT DOCUMENTS

WOA9205736  4/1992  WIPO.

Primary Examiner—Hung X. Dang
Attorney, Agent, or Firm—Quarles & Brady

[57] ABSTRACT

A binocular apparatus for determining pupil dimensions for the eyes of a subject which include an optical imaging apparatus permitting images defining each pupil to be simultaneously transmitted along separate optical paths to a common optical sensing device. The binocular apparatus is useful in measuring anisocoria and in detecting drug abuse and/or opiate addiction. A method for determining pupil dimensions for the eyes is also presented.

24 Claims, 11 Drawing Sheets

Rad = 123 pixels hdia = 250 pixels
vdia = 246 pixels

Rad = 76 pixels hdia = 152 pixels
vdia = 110 pixels (ii)

Rad = 123 pixels hdia = 200 pixels
vdia = 246 pixels

Rad = 120 pixels hdia = 245 pixels
vdia = 240 pixels

APPARATUS FOR DETERMINING PUPIL DIMENSIONS

BACKGROUND OF THE INVENTION (1) Field of the Invention

This invention relates to a pupillometer, that is to say apparatus for determining pupil dimensions for the eyes of a subject, in particular, although not necessarily exclusively, a human subject.

There are many medical applications for the ability accurately to measure pupil size. For example, there are many studies in which measurement of anisocoria (inequality of pupil sizes) has played an important role as a diagnostic test for disease. It is known, for example, that subjects with corneal abrasions, marginal keratitis and acute anterior uveitis demonstrate significantly smaller mean pupillary diameters in the affected eye. Other applications for anisocoria measurement include the diagnosis and localisation of the lesion(s) in Horner's syndrome, as a means for detecting neuro-ophthalmic and ophthalmic disease in newborn infants and in subjects exhibiting Pigmentary Dispersion Syndrome.

In more general terms, observation of the delicately controlled pupil provides a method for observing the mechanisms of the autonomic nervous system. It is known for example that the dynamic parameters of pupillary reflexes (e.g. peak velocity of constriction, latency and amplitude) can provide a useful method of detecting the physiological effects of drug or opiate addiction, e.g. using the Naloxone eye drop test described by Creighton et al. in The Lancet (Apr. 8, 1989), pp 748-750.

(2) Description of the Prior Art

One of the simplest methods of determining pupil size relies upon comparison of the pupil with a series of black dots of various sizes. The inherent subjectivity of this method means that it is suitable only for making crude estimations. Photographic techniques, in which the measurement of the pupil diameter is obtained from an enlarged print or negative, offer a more objective method, but there may still be a degree of subjectivity associated with such manual determinations.

Electronic systems for pupil measurement are known, the simplest of which use a photocell to detect the amount of infra-red radiation reflected by the iris from a nearby source. Such systems allow measurements to be made in total darkness or under controlled levels of illumination. They do, however, require individual calibration for every subject, since the reflectivity of the iris varies with pupil size, and pupil area is also not linearly related to the amount of reflected radiation.

Scanning systems which do not require this recalibration have been devised. Early 'flying spot' scanners mechanically directed a narrow spot of intra-red radiation across the eye, with a photocell detecting the reflected radiation. More recently, electronic image scanners have become popular: instead of scanning the eye itself, its image is projected by a lens onto a detector which is electronically scanned. The simplest of these image scanners comprise single-dimensional arrays of photodiodes which have to be accurately aligned with the pupil diameter. The use of two single-dimensional arrays, mounted orthogonally in the image plane, may obviate this necessity. Although these systems assume that the pupil is circular and have limited capabilities for dealing with eye movements, their fast processing time (e.g. with temporal resolution of up to 10 milliseconds) and comparatively low cost render them attractive tools for many research applications.

Television systems are now most commonly used for image scanning in pupillometry. A modern instrument typically employs a two-dimensional charge-coupled device (CCD) array (usually with 512×512 detector elements) as an image sensor. Each element produces a voltage dependent on its exposure to e.g. infra-red radiation, with detector element voltages being individually interrogated and read out serially onto an output line as a video signal. Older instruments use an electron beam image scanning tube such as the 'Vidicon', where an electron beam is generated at the rear of the tube and deflected across the image electromagnetically or electrostatically and is modulated in accordance with the luminosity of the image, the modulated electron beam being outputted as a video signal. Such tubes, however, require extensive signal processing circuitry to correct for inherent image distortion, which increases their price, and until fairly recently and the advent of solid state sensors, scanning systems have tended to be found only in research institutions because of their high price and high space requirements for their operation.

Monocular measurements of anisocoria, i.e. measurements in which the pupil dimensions for each eye are determined separately, are fundamentally unsatisfactory, since although accommodation and light level (i.e. change in the effective focal length of the eye accompanied by change in pupil size) can be controlled, it is not possible to control the pupillary effects of the higher centres of the brain. Pupil size may therefore alter significantly over time. 'Hippus' or pupillary unrest is also always present; the amplitude of such oscillations is thought to be influenced by factors such as respiratory function and fatigue. Separate measurements of the two pupils at different times cannot therefore provide an accurate determination of anisocoria.

Simultaneous, i.e. binocular measurement of the two pupils is therefore desirable, and simultaneous binocular television systems are known; binocular measurements can alternatively be made photographically.

There are a number of problems associated with such methods. Thus, for example, currently available binocular television pupillometers typically comprise a twin television camera-monitor arrangement, which along with the necessary electronic circuitry requires considerable laboratory space; a dedicated room with controlled levels of illumination and accommodation is invariably a prerequisite.

SUMMARY OF THE INVENTION

The present invention is based on the finding that binocular apparatus incorporating a single optical sensing means may be used to determine pupil dimensions to a good degree of accuracy, with equipment requirements such that the apparatus may readily be made to be portable.

Thus, according to one aspect of the invention, there is provided binocular apparatus for determining pupil dimensions for the eyes of a subject, said apparatus comprising optical imaging means whereby in use images defining each respective pupil may be simultaneously transmitted along separate optical paths to a common optical sensing means.

Such apparatus, by permitting simultaneous determination of pupil dimensions using a single optical sensing means avoids both the potential sources of error introduced by monocular methods and the cost and space requirements of dual sensing systems such as video cameras or the like with attendant image recording/processing means et.

The use of a separate optical train for imaging each pupil may advantageously permit a higher level of magnification than is typically obtainable with, for example, previously proposed apparatus with which the subject is monitored full-face via a single detector and a single optical path, with consequent enhancement of sensitivity.

The optical sensing means may, for example, comprise a two-dimensional array of charge-coupled devices, e.g. as in a CCD video camera selected to have appropriate sensitivity at the wavelength chosen for the pupil dimension determination, or may comprise a photographic film, e.g. a Polaroid film.

Means may be provided for dividing the sensor area of the optical sensing means into two separate areas for receiving images of the two eyes without overlap. Such means may, for example, comprise a divider plate extending perpendicularly from the sensor area so as to enhance optical separation of the two optical paths.

The apparatus may include means whereby the eyes are irradiated with e.g. low-intensity infra-red radiation, the imaging means being such as in use to produce images of the infra-red radiation reflected from the iris of each eye and thereby defining each pupil. The optical sensing means in such embodiments of the invention is advantageously a CCD video camera.

Alternatively the apparatus may include e.g. electronic flashgun means having optical fibres leading therefrom whereby in use each eye may be irradiated. The optical sensing means in such embodiments of the invention may, for example, be a photographic film, e.g. in association with shutter means which control the exposure thereof and which have an operating mechanism linked to switching means for the flashgun means whereby operation of the flashgun means is triggered by actuation of the shutter means.

The apparatus of the invention preferably also incorporates background illuminating means for illuminating each eye with a controlled and uniform amount of visible light, e.g. from a low wattage light bulb, so as in use to provide an ambient illumination level.

Since interpupillary distances inevitably vary from subject to subject the apparatus advantageously includes adjusting means permitting adaptation to the interpupillary distances of individual subjects, preferably without altering the optical path length of the apparatus. This may, for example, be achieved by mounting the optical components of each optical path (e.g. objective lens or lenses, mirrors etc.) on a respective base member, the two base members being moveable towards and away from each other, e.g. by means of a threadedly engaging screw shaft having two oppositely threaded portions for engaging the respective base members. To ensure that the optical path length from pupil to its image should remain constant regardless of any change in the spacing of the two optical paths there are preferably provided optical path length compensating means whereby the position of the imaging means may be adjusted to compensate for any change in the optical path length that might otherwise occur upon adjusting the spacing of the optical paths. To this end the optical sensing means may be mounted on a further base member connected to the aforementioned base members by a mechanical linkage whereby movement of said base members causes corresponding compensating movement of the optical sensing means base member.

Alternatively the optical paths may comprise fixed lens systems etc. each carrying a periscopic eyepiece which is mounted so as to be axially moveable about its respective optical path. This permits the distance between the eyepieces to be adjusted without altering the overall optical pathlength, which in all cases will be the sum of the pathlengths of the principal optical path and the periscope.

Where the optical sensing means comprise e.g. a CCD video camera, the output thereof may, if desired, be monitored by a TV monitor, and may be processed directly by appropriate image processing means. Preferably, however, recording means such as a video recorder are provided to record the output for subsequent image processing. This is advantageous since it permits the image processing to be carried out separately, for example at a central laboratory, remote from the test site, thereby reducing equipment requirements at the test site.

Viewed from another broad aspect the invention provides a method for determining pupil dimensions for the eyes of a subject comprising simultaneously projecting images defining each respective pupil along separate optical paths onto a common optical sensing means.

Where the optical sensing means comprise e.g. a CCD video camera, the output thereof is preferably recorded before subsequently being processed. The image processing is preferably performed by a computer and is preferably carried out on a frame obtained by a framegrabber card. The image processing may include a number of techniques, such as image enhancement, automatic measurement of pupil dimensions in terms of area and/or maximum and minimum dimensions, and by means of a circle-fitting algorithm variation in pupil shape from absolute circularity may be determined.

The invention will now be described by way of example and with reference to the accompanying drawings, in which:

DESCRIPTION OF THE PREFERRED EMBODIMENTS

Figure 1:
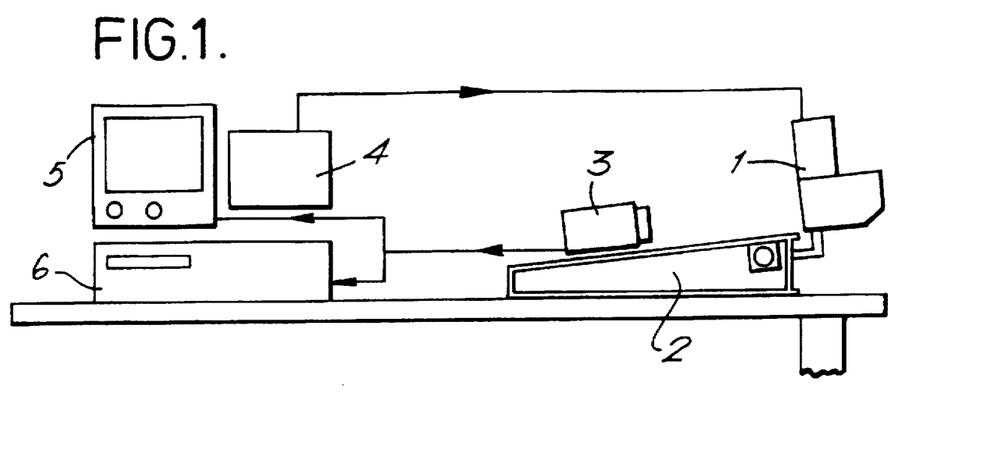
FIG. 1 is a schematic representation of elements of apparatus according to a first embodiment of the invention.
Figure 2:
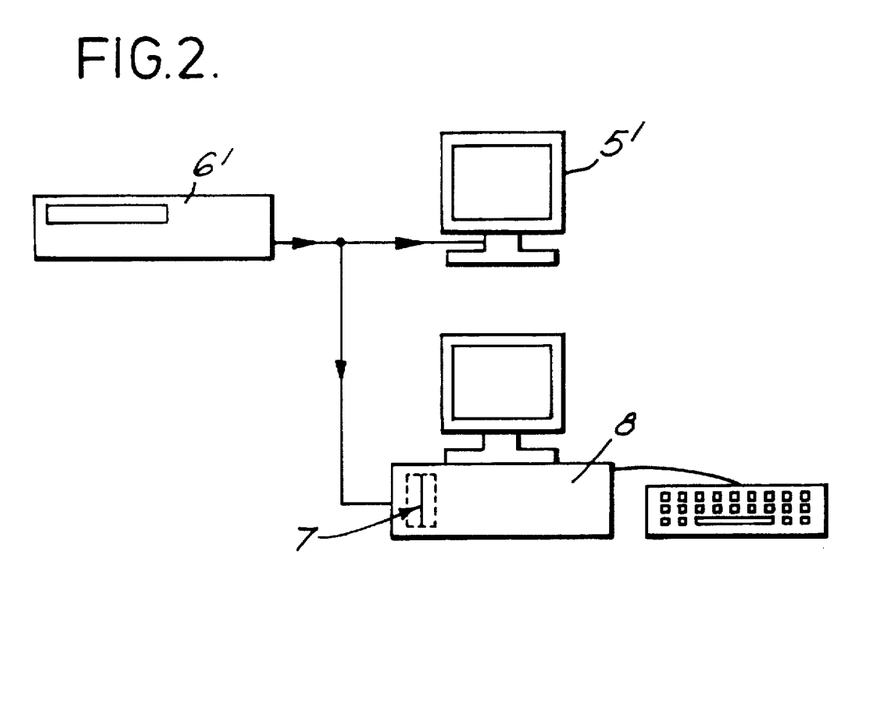
FIG. 2 is a schematic representation of further elements of apparatus according to said first embodiment of the invention.

FIG. 1 illustrates in block schematic form the principal elements of a first embodiment of apparatus according to the invention as it may be provided in situ, e.g. in an out-patients department or a clinic. The apparatus comprises a combined face rest and illumination means 1, a bench support 2, an imager head 3, timer and infra-red control means 4, TV monitor 5 and video recorder 6. Detailed operation of this embodiment will be described further below, but in summary the face of a subject is placed in the face rest 1 and the eyes are subject to illumination by infra-red means controlled by the timer and control means 4. Images defining both pupils are simultaneously observed by sensing means 3 and the results outputted to the video monitor 5 and video recorder 6. These are the only high-level components that need be provided in situ in the clinic, out-patients department or the like where the testing is conducted. The results can be processed remotely, in a manner to be described in further detail below, by the apparatus shown in FIG. 2 which may be provided at, for example, a central laboratory. This apparatus includes a video player 6' for playing back the tape recorded by the recorder 6 of FIG. 1. The output of video player 6' goes to second video monitor 5' and, via a framegrabber card 7, to a computer 8 for image processing and to determine final pupil dimensions in a manner to be described further below. It will of course be appreciated that whilst FIGS. 1 and 2 have been described as separate remote halves of the apparatus, they need not be so and may be combined into a single apparatus.

Figure 3:
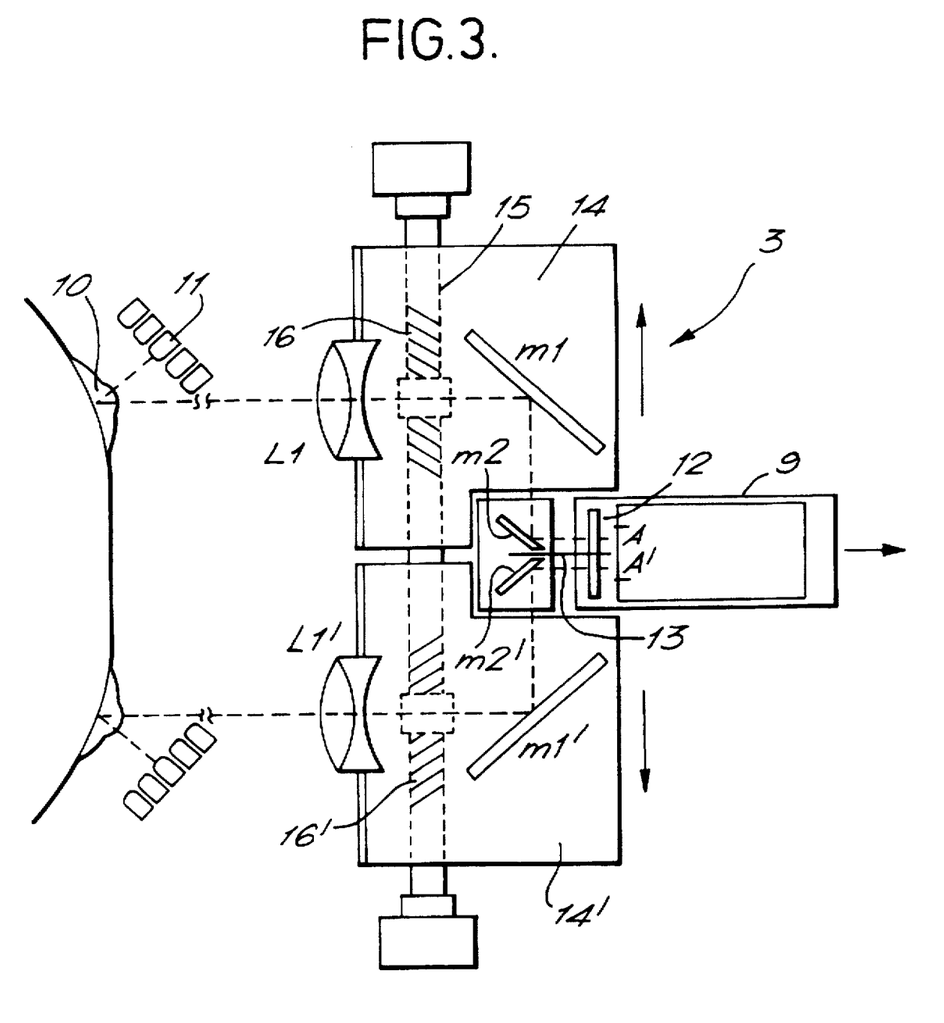
FIG. 3 is a plan view showing the optical paths and sensing means of said first embodiment of the invention.

FIG. 3 illustrates the optical system of the aforesaid imager head 3; this is a double-lens imaging system designed to product images of both pupils projected onto the detector elements of a CCD television camera 9, at 0.4 magnification. Identical optical paths are provided for each eye 10, and each eye 10 is illuminated by respective infra-red illuminating means 11 as will be described further below. Each optical path includes an objective lens L1 (L1') (F=75 mm) which projects an infra-red image of a respective eye onto a respective half A,A' of the sensor area of camera 9 via front silvered mirrors m1, m2 (m1',m2') and infra-red pass filter 12. Overlap of the images on the sensor is prevented by the provision of a divider blade 13 extending perpendicularly therefrom and between mirrors m2,m2'.

The mirrors m1,m2 (m1',m2') are mounted on mirror platforms 14,14'. The fields of view of the two optical paths are relatively narrow, and thus means are provided to adjust the distance between their optical axes to allow for variation in interpupillary distance from subject to subject; typically such distances range from 55 mm to 70 mm. This adjustment is achieved by mounting the mirror platforms 14,14' on a lead screw 15, the lead screw 15 being provided with oppositely threaded portions 16,16' which threadedly engage the respective mirror platforms 14,14'. In this way, by appropriate rotation of the lead screw 15 the mirror platforms 14,14' may be caused to move together or apart to reduce or increase the distance between the optical axes as required.

Figure 4:
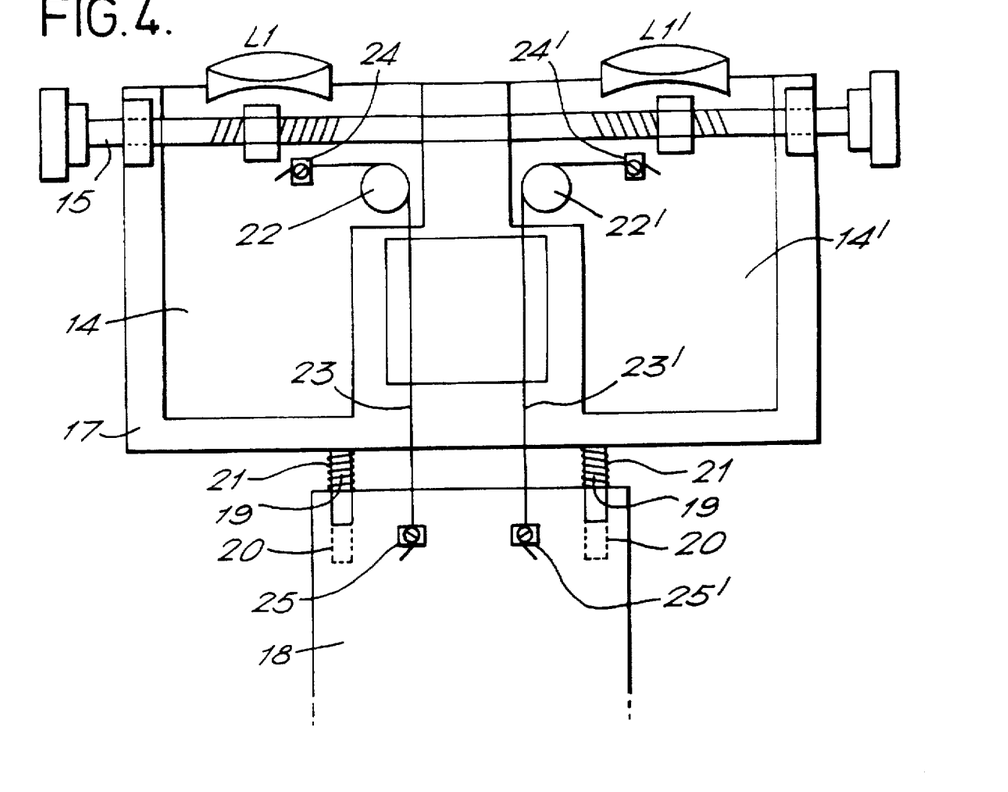
FIG. 4 is schematic underside view corresponding to FIG. 3.

It will be appreciated that moving mirror platforms 14,14' apart or together changes the length of the optical path between mirrors m1,m1' and m2,m2'. Since the total optical path should desirably remain constant in length, this change may be compensated for as shown in FIG. 4. Mirror platforms 14,14' are mounted on a base 17 and are adapted to move together and apart via lead screw 15 as previously described. Camera 9 is mounted on a camera base 18, and camera base 18 is mounted to the mirror base 17 via a pair of shafts 19 extending from base 17 perpendicularly to the direction of movement of the mirror platforms 14,14'. Shafts 19 are slidably received within bores 20 provided in the camera base 18. Springs 21 are provided around each of the shafts 19 between the camera base 18 and the mirror base 17. Each mirror platform 14,14' is provided with a pulley 22,22' and cable 23,23' is passed around each pulley from a fixing point 24,24' on each mirror platform to a respective fixing point 25,25' on the camera base. The effect of this arrangement is that when the mirror platforms 14,14' move apart, the cables 23,23' act to pull the camera base 18 toward the mirror base 17 against the springs 21. On the other hand, when the mirror platforms 14,14' move together, springs 21 urge the camera base 18 away from the mirror base 17. Thus there is provided an optical path length compensating arrangement.

Figure 5:
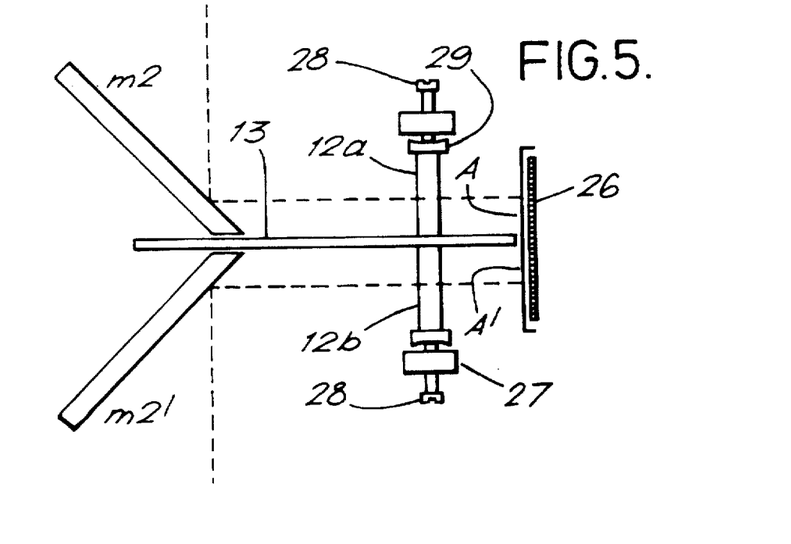
FIG. 5 is a detailed view of part of the sensing means of said first embodiment of the invention.
Figures 6, 7:
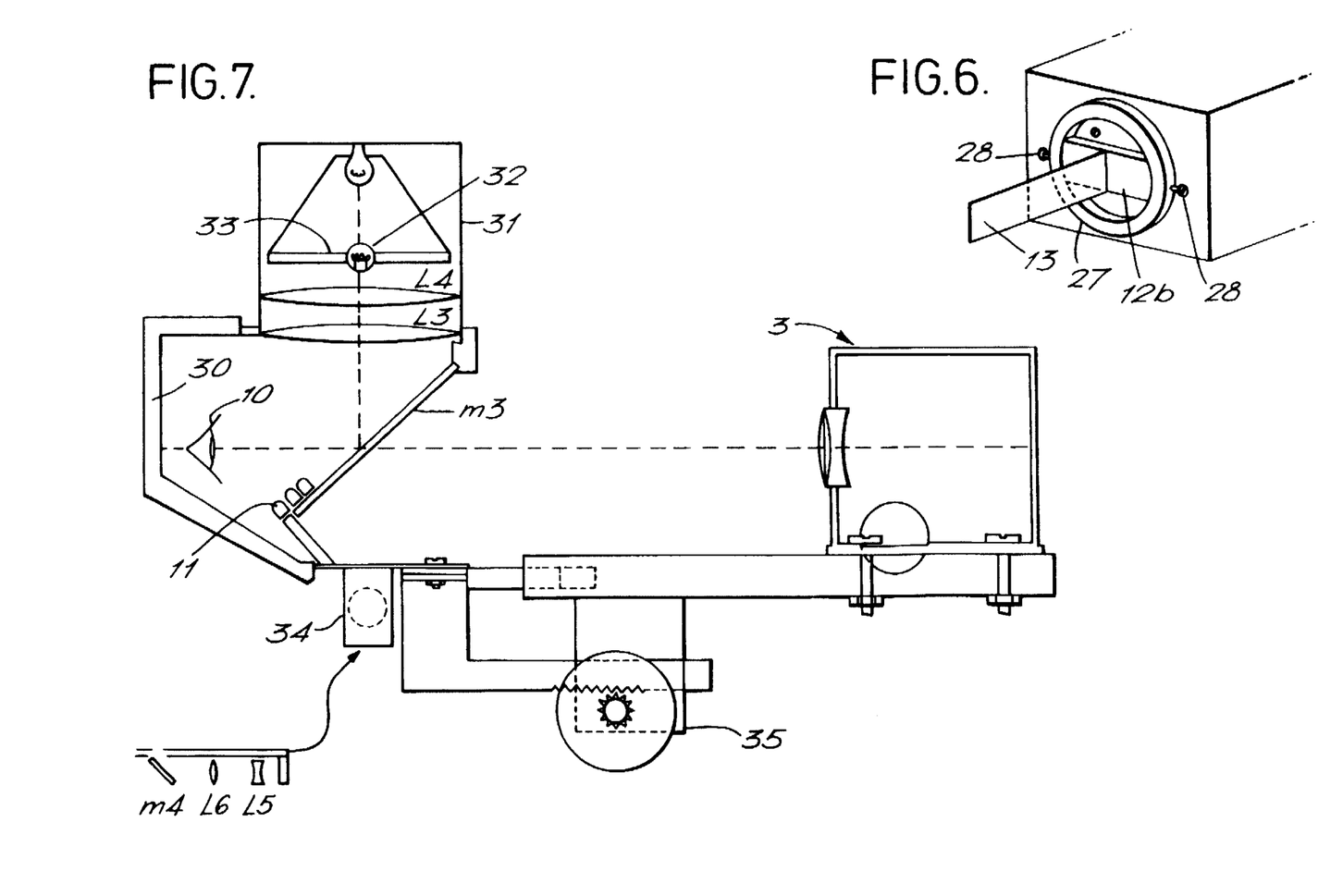
FIG. 6 is a perspective view corresponding to FIG. 5.
FIG. 7 is a side view showing in particular the illumination means of said first embodiment of the invention.

FIGS. 5.and 6 illustrate in more detail the aforesaid apparatus in the region of the sensor area of the CCD camera 9, in particular the blade 13 which divides the sensor area of the CCD camera 9 into two halves A,A'. The blade 13 is formed of 0.1 mm thick steel painted matt black, and is preferably positioned as close as possible to the surface of the sensor area 26 without actually being in contact therewith, to avoid damage to the sensor. The infra-red pass filter 12 is in fact formed of two halves 12a,12b provided on either side of the blade 13. Filters 12a,12b are received within an outer holding ring 27 and serve to "clamp" the blade 13 in place. Fine adjustment of the position of the divider blade 13 may be made by means of adjusting screws 28 which act on filters 12a,12b via neoprene pads 29. The end of the blade 13 remote from the sensor is slidably received in a gap provided between the edges of mirrors m2,m2', which are bevelled to 45° to ensure that mirrors m2,m2' are not field stops for the final images. A light-tight external case (not shown) and the majority of component parts of the camera are made with anodised Dural which is painted matt black on all internal surfaces to reduce stray reflections which would otherwise reduce image contrast.

FIG. 7 illustrates in more detail the face rest and illumination means of the aforesaid apparatus. The face rest comprises a rectangular foam-padded enclosure 30, one end of which is cut away to accept the forehead and cheeks of a subject. Inside enclosure 30 is a half-aluminised mirror m3, positioned with its surface 45° to the optical axes of the eyes. Above mirror m3 is provided an illumination head 31 comprising fixation lamp 32 and a surrounding illuminating screen 33. The lamp 32 and screen 33 are placed optically at 50 cm from the subject via lenses L3, L4 and illuminate the eyes via mirror m3. Five GaAlAs infra-red emitting diodes (IREDS) 11, positioned at the lower corners of mirror m3, irradiate each eye. The measured irradiance at the eye from these IREDS is only 40 $Wm^{-2}$, while the maximum permissible near infra-red irradiance for continuous exposure of the anterior eye is 100 $Wm^{-2}$.

Equal reflection-transmission characteristics of mirror m3 extend well into the near infra-red region of the spectrum, allowing the infra-red irradiation which is reflected from each iris to pass therethrough and into the objective lenses of the imaging head 3. When the pupil images are recorded, information about the time and light level is outputted onto a display 34 mounted on the face rest. The displayed information is relayed into the field of view of the imaging head 3 by means of an optical train comprising lenses L5, L6 and mirror m4. A black velvet zip-up hood (not shown) encapsulates the imager and illumination head, preventing extraneous light from entering the subject's eyes. When the hood is in position, the subject can see only the reflection of the screen 33 and the fixation lamp 32 in the mirror m3. A rack-and-pinion mechanism 35 is provided to permit fine adjustment of the image at the imaging head 3.

Figure 8:
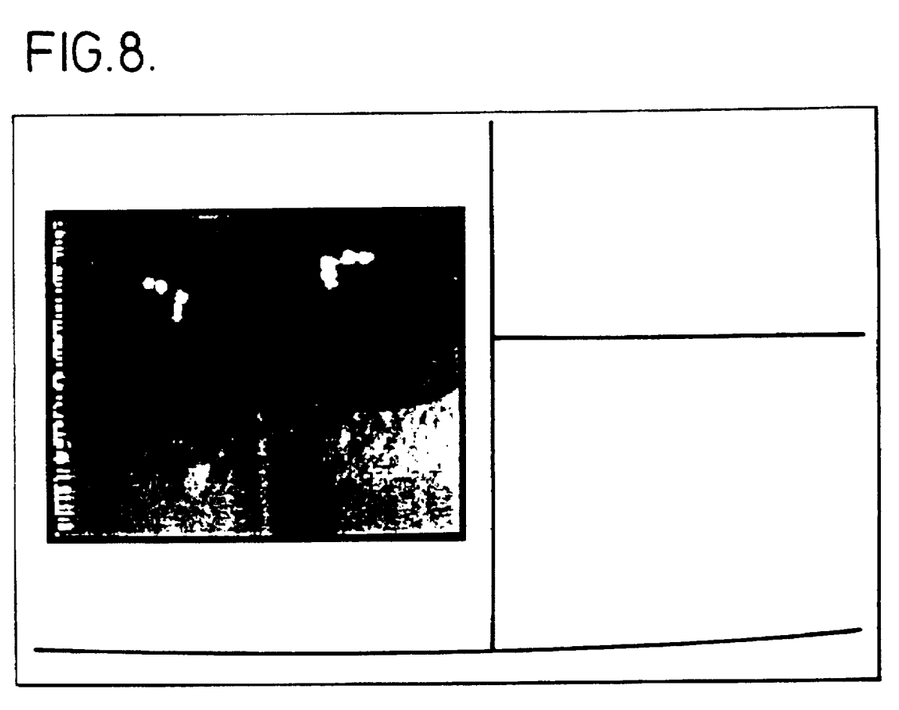
FIG. 8 illustrates a typical image display for the two pupils of a subject, obtained using apparatus according to said first embodiment of the invention.

In an example of clinical use of such an embodiment of apparatus according to the invention, the CCD video camera output is connected to a video recorder. The video tape is subsequently replayed and a video framegrabber (Imaging Technology VS100) used to digitalise the images for digital processing. This system samples each line of the video signal at 768 discrete points across a single horizontal scan line, 512 lines per frame, with 8 bit ADC resolution (256 grey levels). The digitalised pupil images are written to a disk file for subsequent analysis by programmes written in C, while the images of the pupils may be displayed on e.g. a VGA IBM PC monitor, as shown in FIG. 8—the slight distortion which is apparent is due to a difference in the aspect ratio between the video framegrabber and the computer display and does not affect the analysis.

Figure 9:
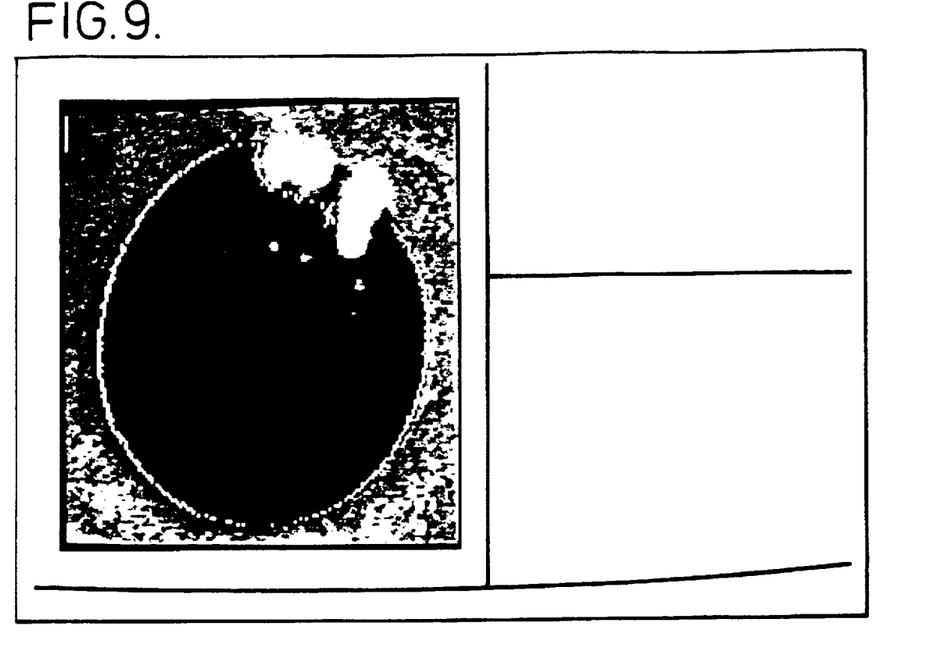
FIG. 9 illustrates raw pupil edge data points obtained using apparatus according to said first embodiment of the invention.
Figure 10:
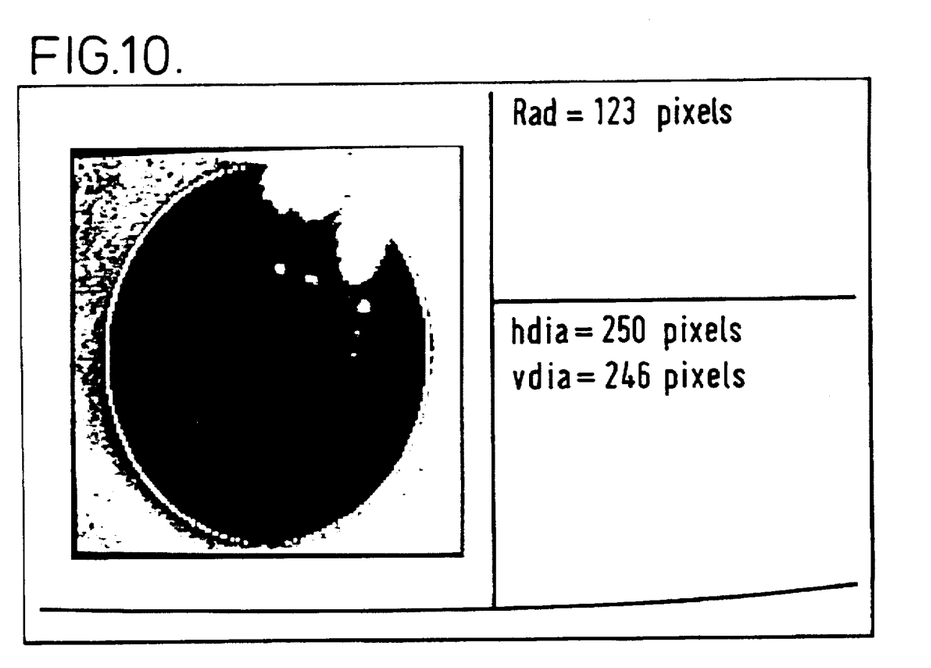
FIG. 10 illustrates a circle fitted to the data of FIG. 9.

In analysing the digitalised images to identify the pupil-iris boundaries, a threshold level is set between the maximum and minimum grey levels in the image; specular reflections have been found to correspond to grey levels above 100 and are rejected from the process. The maximum should therefore correspond to the iris and the minimum to the pupil. The relative position of the threshold between these two extremes is set manually, and held constant for any given subject. The left edge of the pupil is found by counting the number of pixels forwards from the start of each line, until the 'grey level' of the pixel under examination is less than that of the threshold. The second pupil edge is established as the last transition from pupil grey level to iris grey level on the same line. False pupil-iris transitions in between, e.g. caused by isolated reflections in the cornea, are thus ignored. Reflections which occur on the borders themselves cannot be overcome in this way, and the 'outline' of the pupil which is arrived at by this thresholding technique can be very much distorted in shape, e.g. as shown in FIG. 9. To remove the effects of local distortions on the pupil size determination, a circle is fitted to all of the edge points. A threshold algorithm is used to label all the points on the pupil image boundaries, producing a 'raw' outline of the pupil. The horizontal and vertical extreme edge positions of the 'raw' pupil outline are used to calculate the radius and centre of the fitted circle. For precise fitting of the circle to the raw pupil outline, the sums of the differences between the two are used as a measure of the 'error' of the fit, which is then minimised by varying the position and radius of the circle. When the best fit to the 'raw' data has been found, pupil boundary data points are considered artefactual and removed if they deviate by more than 10% from the fitted circle. The fitting procedure is then repeated to obtain the best fit to the remaining data points, e.g. to give a result as shown in FIG. 10. The standard deviation of the final fitted circle to the raw edge points, minus the artefactual points, is then computed and used as an indicator of the circularity of the pupil.

Figure 11:
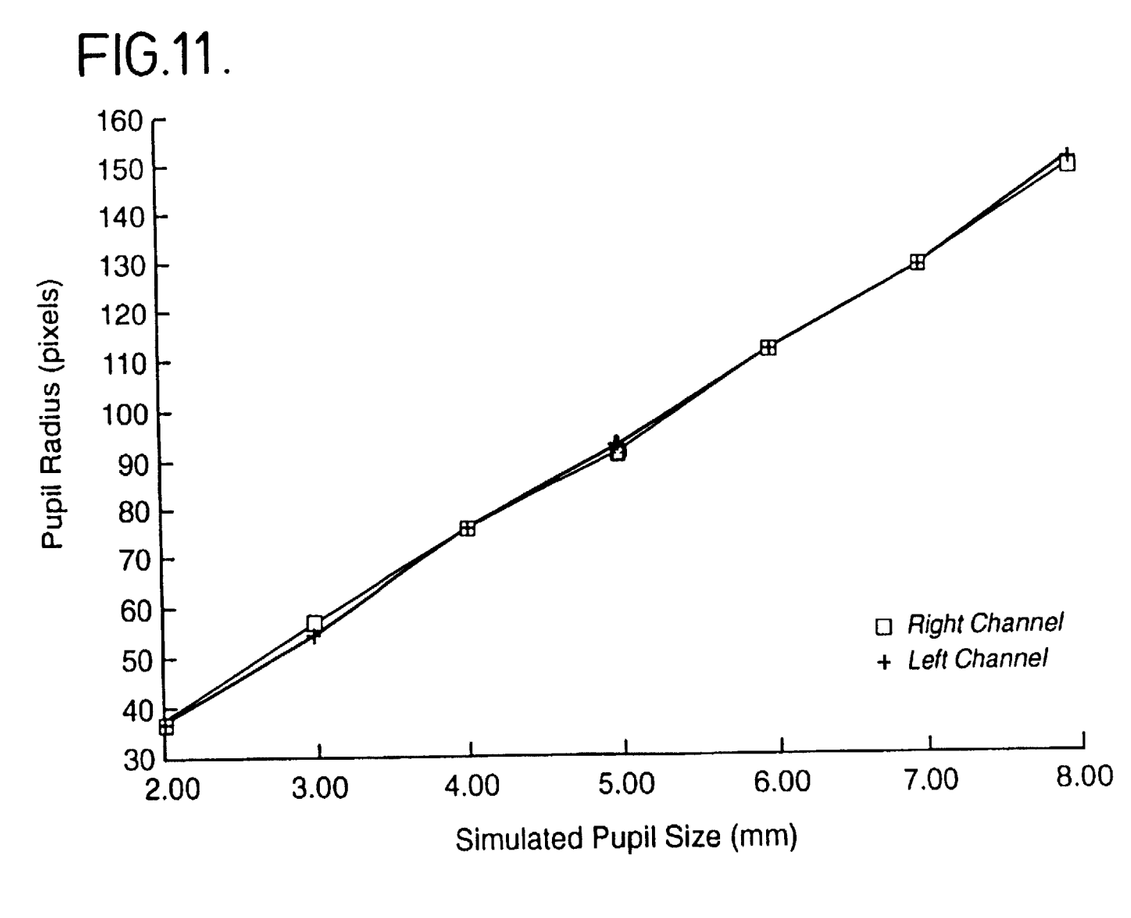
FIG. 11 is a calibration graph for apparatus according to said first embodiment of the invention.

The accuracy of the above-described apparatus is limited by the horizontal and vertical resolutions of the CCD camera 9. Typical conventional empirically determined values of limiting display line spacial resolutions are 420 lines vertically and 380 lines horizontally. Assuming the image defining a pupil is optimally focused, the CCD sensor and imaging system could theoretically resolve the diameter of a pupil to ±0.053 mm horizontally and ±0.036 mm vertically. A detailed examination of the accuracy and linearity of the system was carried out by the application of the circle-fitting routines to video images of several simulated pupils punched in thin, crisp, light blue paper ranging in diameter from 2 to 9 mm in 1 mm increments. The apparatus was found to be spatially linear with a coefficient of correlation of 0.999 and a regression factor of 19.1 pixels/mm (standard error=0.3 pixels) as shown in FIG. 11.

Figure 12:
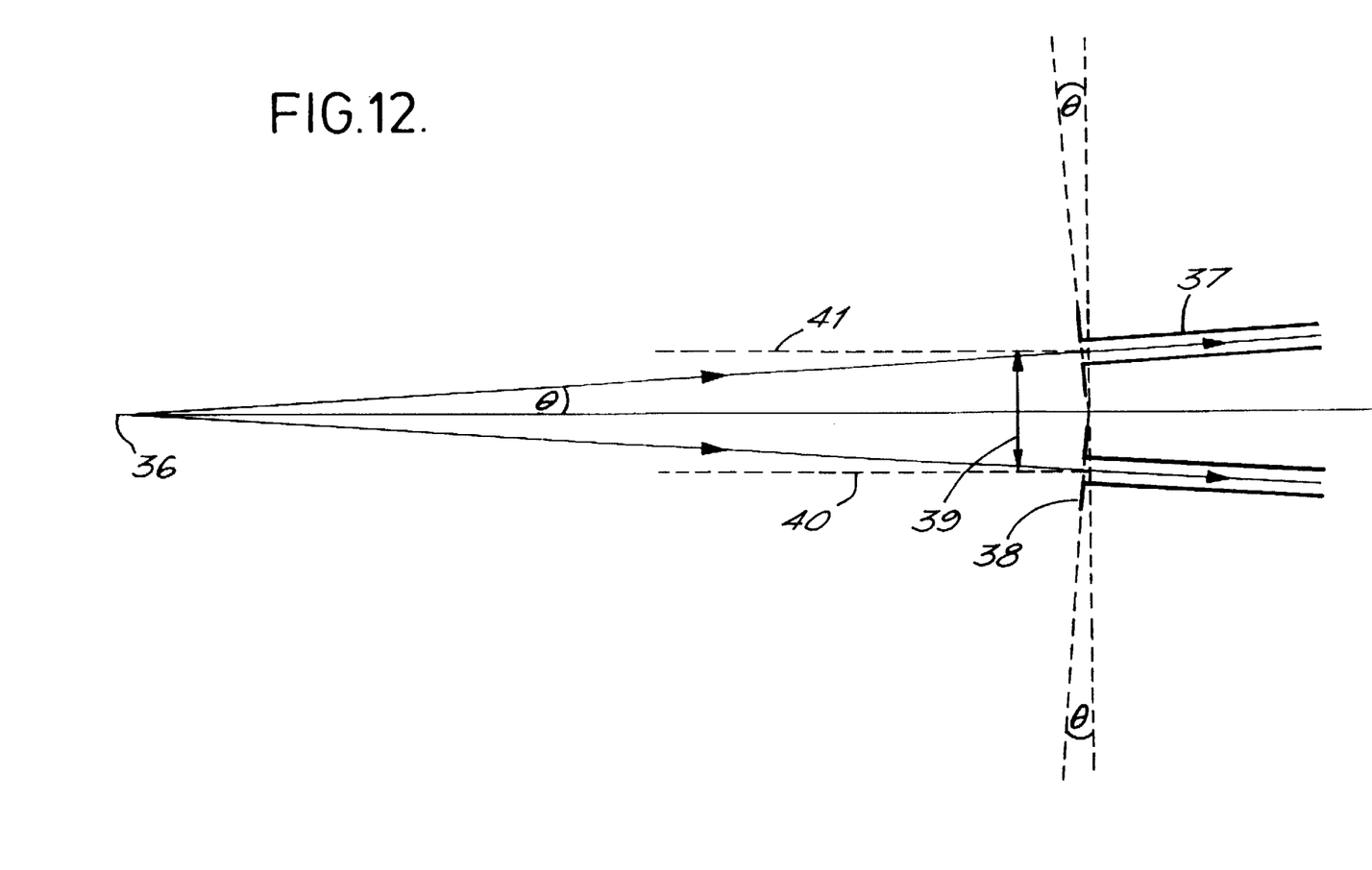
FIG. 12 shows apparatus for investigating the effect of oblique images.

Three other possible causes of spatial non-linearity were also investigated: (i) placing a single paper hole at different points away from the optical axis of each of the two imaging systems (ii) misfocusing the image and (iii) tilting the paper hole about its own central axis. The fixation lamp is optically at 50 cm from the subject (checked using a single lens reflex camera focused at 50 cm), and its proximity to the subject necessitates a degree of convergence of the gaze. The apparatus shown in FIG. 12 was used to investigate the degree of 'obliqueness' of the image likely to be encountered when measuring subjects by viewing the fixation point 36 through sighting tubes 37 and simulated pupils 38 at a typical interpupillary spacing 39 between the optical axis of the left channel 40 and the optical axis of the right channel 41. It was found that the angle of tilt '8' is less than 5.7° for the range of inter-pupillary distances over which the optical system will operate. The error in radius measurement at this angle was found to be less than 0.25%. Variation of the off-optical axis position of the image both vertically and horizontally on the sensor caused deviations of less than 1% from the radius obtained with an image placed centrally on the optical axis.

The effect of misfocusing was studied using a single simulated pupil placed at various distances nearer to and further from the position of optimum focus. A measurement of pupil size can be expected to deviate from that obtained at the position of optimum focus by a degree dependent on whether the pupil is placed between the objective lens and the optimum focus (in the near field) or further away from the objective lens than the position of optimum focus (in the far field). In the near field, errors are not as serious as those in the far field. In the former, errors increase at a rate of less than 1% per cm displacement from the optimum focus position, causing the instrument to overestimate the pupil dimensions. In the case of the latter, this rate is −7% per cm, causing the instrument to underestimate the pupil dimensions. It is clearly more desirable to have the subject too near to rather than too far from the pupillometer.

In practice, it is not uncommon that one pupil is not optimally focused on the image sensor. For this reason, the variability in the measured anisocoria for 12 healthy volunteers was plotted, making 10 measurements of the anisorcia at each of 3 discrete light levels. The absolute anisocoria is expressed as a fraction of the mean diameter of the two pupils at any given time, since the results indicate a high degree of correlation between this 'fractional anisocoria' for different light levels at any given time point (average coefficient of correlation=0.82). The variability in the measurement of the anisocoria for any given subject was found by calculating the standard deviation of the 30 fractional anisocoria measurements for that subject. The variabilities for all 12 subjects were found to be within the range 1.5%–2.1% for the three light levels, the largest variabilities being found in the largest pupils. These represent a variability of less than 0.1 mm in the measurement of a pupil with a 5 mm radius circle fitted to it, increasing to 0.2 mm for 1 mm radius.

Figure 13:
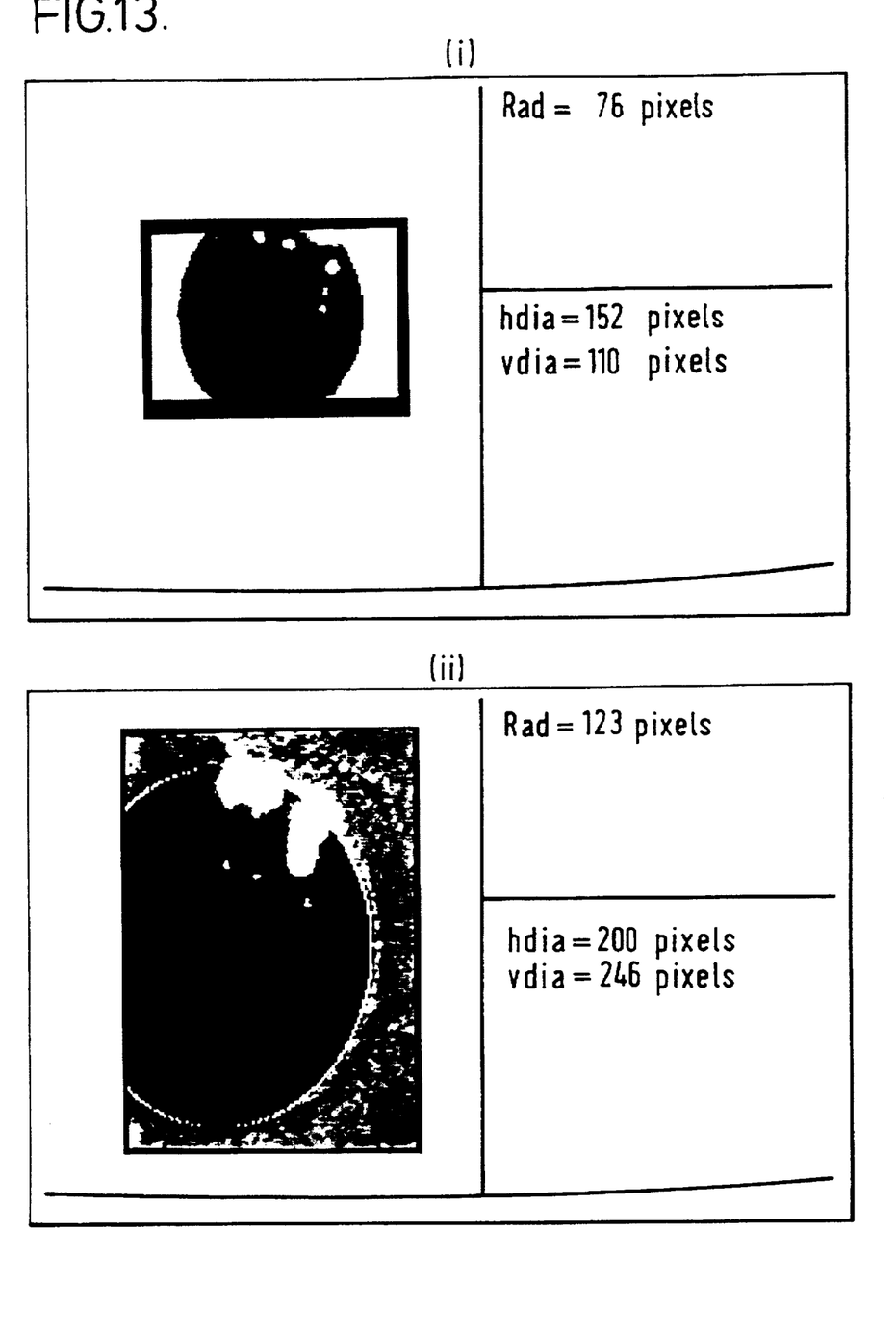
FIG. 13 illustrates the effects of missing portions of the image.
Figure 14:
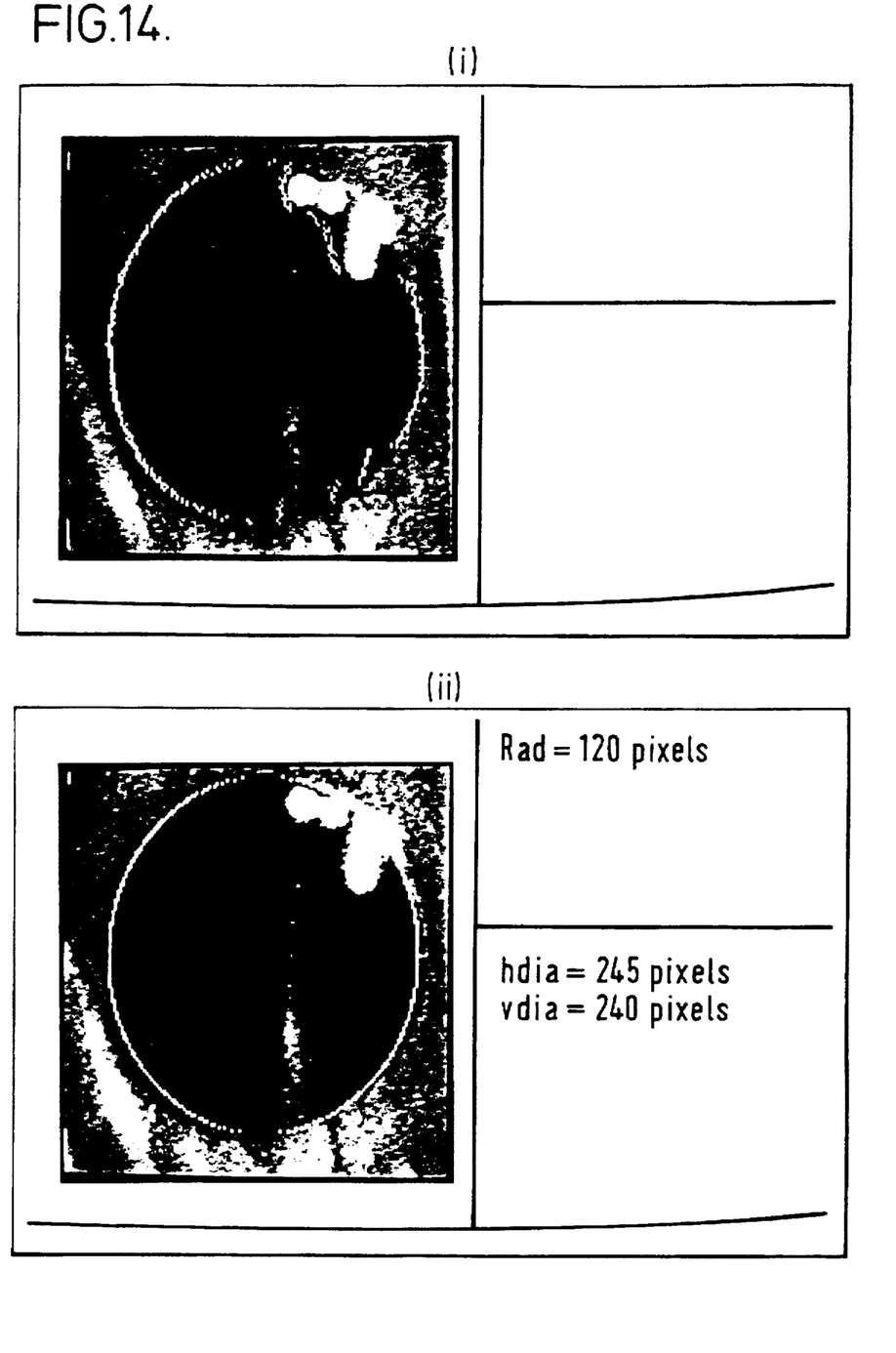
FIG. 14 illustrates the effects of extraneous elements in the image.

The circle fitting algorithm is judged to provide a 'successful fit' to the pupil image if the standard deviation of the fit is less than 4 pixels for largest pupils (radii greater than 90 pixels), and less than 2 pixels for smaller pupils (radii less than 60 pixels). Larger pupils have greater standard deviations of fit than smaller pupils, owing to the greater resolution of the difference between the fitted circle and the pupil image. In a representative study, a total of 2360 'successful fits' were made to the 2400 pupil images from 40 opiate-dependent individuals and 720 measurements on 12 normal volunteers (60 measurements per individual). The 40 that failed occurred mainly at the beginning of the study, and were due to operator errors in focusing. The fitting routine is capable of 'recognising' pupil images that are partially obscured, as long as no more than about a third of the pupil image is missing (as shown in FIGS. 13 (*i*) and (*ii*)) or obscured by extraneous elements (as shown in FIG. 14 (*i*), the best fit result being shown in FIG. 14 (*ii*)). The time taken to fit a circle is less than 10 seconds, using a 386 processor running at 25 MHz.

Figure 15:
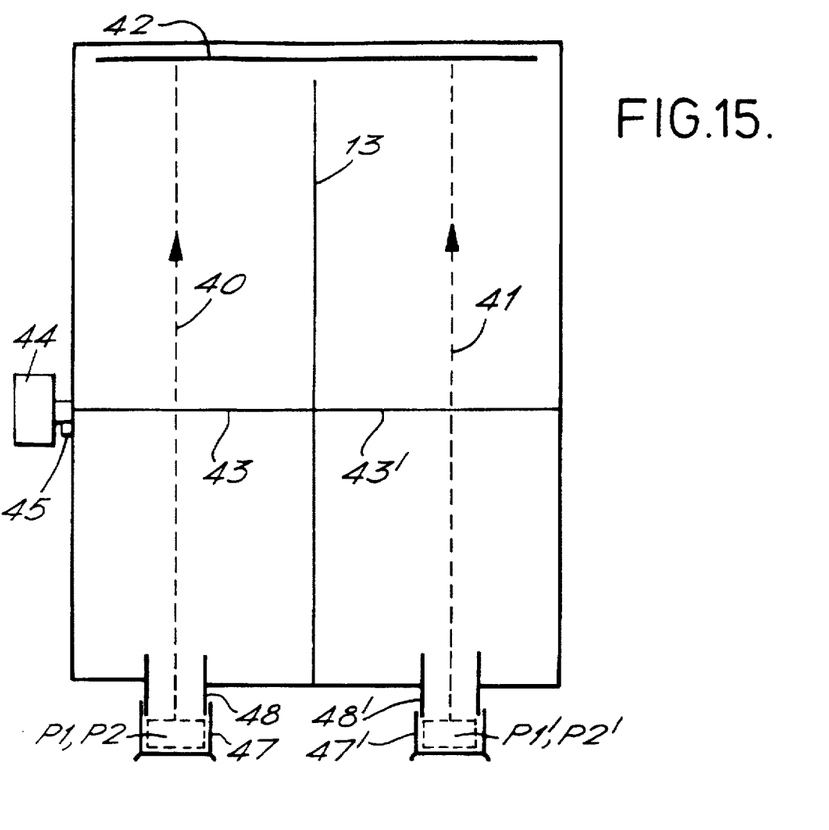
FIG. 15 is a schematic representation from above of elements of apparatus according to a second embodiment of the invention.
Figure 16:
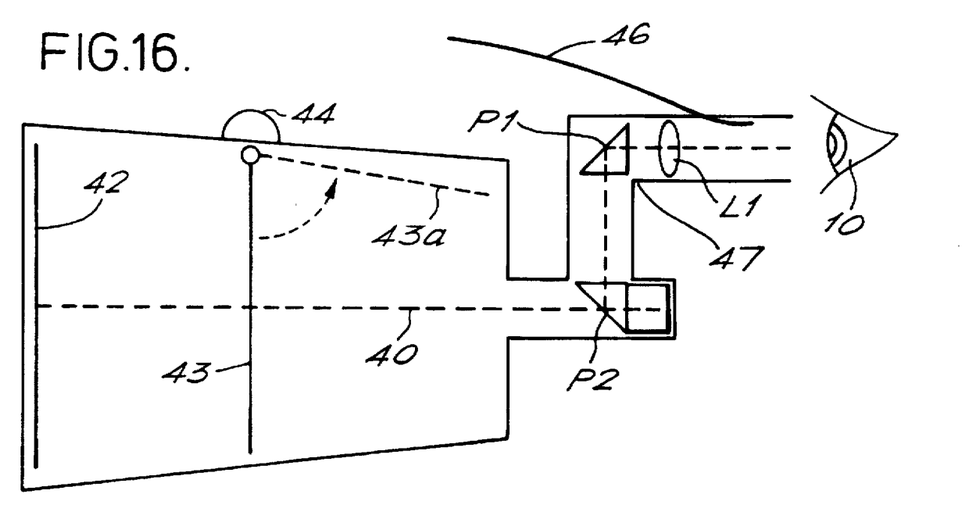
FIG. 16 is a schematic representation from one side of the apparatus of FIG. 15.

FIGS. 15 and 16 illustrate in schematic form the principal elements of a second embodiment of apparatus according to the invention. In this embodiment the optical sensing means comprise a Polaroid film 42, exposure of which is controlled by shutters 43,43' positioned on either side of divider 13 between left and right optical axes 40 and 41 (shutter 43 is also shown in open position at 43a in FIG. 16). The shutters 43,43' are operated by turning knob 44, this also actuating switch 45 which triggers an electronic flashgun (not shown), light from which is piped through 12-stranded optical fibre bundles 46(46') to periscopic eyepieces 47,47' and thus to each eye 10. Ambient illumination is provided by a 6 volt 4 watt lamp (not shown) positioned between the electronic flashgun and the entry points to the optical fibre bundles 46(46').

The periscopic eyepieces 47,47' are rotatable in light-tight manner about tubes 48,48' on the main body of the apparatus so as to permit adjustment for subjects with differing inter-pupillary distances, without altering the overall optical path length of the apparatus. In addition to prisms P1, P1' and P2, P2' the eyepieces 47,47' contain objective lenses L1 (L1'), which are both Schneider Componar lenses (F=75 mm). These project images defining the respective pupils onto separate halves of Polaroid film 42, the image and objective distances being such as to give an overall magnification of 3.

It will be appreciated that pupil dimensions may be determined manually from photographic film obtained using apparatus such as that shown in FIGS. 15 and 16. Alternatively the photographed images may be analysed digitally, e.g. using a video camera and computerised image processing means, for example as herein before described for the apparatus of FIGS. 1-7.

We claim:

1. Binocular apparatus for determining pupil dimensions for the eyes of a subject, said apparatus comprising optical imaging means whereby in use images defining each respective pupil are simultaneously transmitted along separate optical paths onto separate areas of a common optical sensing means, said apparatus further comprising a divider positioned between said separate optical paths and closely adjacent to said optical sensing means so as to enhance optical separation of said areas and the optical paths leading thereto.

2. Apparatus as claimed in claim 1 wherein the optical sensing means comprises a two-dimensional array of charge-coupled devices.

3. Apparatus as claimed in claim 2 including means for irradiating each eye with infra-red radiation whereby in use infra-red images defining the respective pupils are focused substantially at said array of charge-coupled devices.

4. Apparatus as claimed in claim 3 wherein said irradiating means comprise infra-red emitting diodes.

5. The apparatus as claimed in claim 2 wherein the optical sensing means includes a CCD video camera.

6. The apparatus as claimed in claim 5 further comprising a video tape recorder including a video tape whereby the tape can be processed at a site remote from the recording site.

7. Apparatus as claimed in claim 1 wherein the optical sensing means comprises a photographic film.

8. Apparatus as claimed in claim 7 including electronic flashgun means having optical fibers leading therefrom such that in use each eye is irradiated.

9. Apparatus as claimed in claim 8 including shutter means interrupting the two optical paths and having an operating mechanism linked to switching means for said flashgun means whereby the flashgun means are triggered when said shutter means are opened.

10. Apparatus as claimed in claim 1 including means for illuminating each eye with a controlled and uniform amount of visible light so as in use to provide an ambient illumination level.

11. Apparatus as claimed in claim 1 including means whereby the apparatus is adaptable to the interpupillary distances of individual subjects while maintaining a constant optical path length.

12. Apparatus as claimed in claim 11 wherein said adjusting means comprise periscopic eyepieces mounted so as to be axially moveable about each optical path.

13. The apparatus as claimed in claim 1 further including a computerized image processing means to afford automatic determination of the pupil dimensions.

14. Apparatus as claimed in claim 1 wherein said divider comprises a divider plate extending perpendicularly from a position closely adjacent to said optical sensing means.

15. A method for determining pupil dimensions for the eyes of a subject comprising simultaneously projecting and separating images defining each respective pupil along separate optical paths onto separate areas of a common optical sensing means.

16. A method as claimed in claim 15 wherein the output from the optical sensing means is subjected to computerized image processing to afford automatic determination of the pupil dimensions.

17. A method as claimed in claim 16 wherein the computerized image processing includes a circle-fitting algorithm.

18. A method as claimed in claim 17 wherein the output from the optical sensing means is recorded on video tape for processing at a site remote from the recording site.

19. A method as claimed in claim 16 wherein the output from the optical sensing means is recorded on video tape for processing at a site remote from the recording site.

20. A method as claimed in claim 15 wherein the images from the optical sensing means are placed on a photographic film.

21. A method as claimed in claim 20 wherein the resulting photographic images are subsequently analyzed digitally.

22. A method as claimed in claim 15 including the detection of drug abuse.

23. A method as claimed in claim 22 including the detection of opiate addiction.

24. A method as claimed in claim 23 wherein the opiate addiction includes a Naloxone eye-drop test.

* * * * *